United States Patent
Malyska et al.

(10) Patent No.: US 7,767,436 B2
(45) Date of Patent: Aug. 3, 2010

(54) REDUCING TIME TO RESULT FOR BLOOD BANK DIAGNOSTIC TESTING

(75) Inventors: Harry Malyska, Coral Springs, FL (US); Paula Howard, Boynton Beach, FL (US)

(73) Assignee: Micro Typing Systems, Inc., Pompano Beach, FL (US)

( * ) Notice: Subject to any disclaimer, the term of this patent is extended or adjusted under 35 U.S.C. 154(b) by 628 days.

(21) Appl. No.: 10/582,887

(22) PCT Filed: Dec. 17, 2004

(86) PCT No.: PCT/US2004/042531

§ 371 (c)(1),
(2), (4) Date: Jun. 18, 2007

(87) PCT Pub. No.: WO2005/064347

PCT Pub. Date: Jul. 14, 2005

(65) Prior Publication Data

US 2007/0298446 A1      Dec. 27, 2007

Related U.S. Application Data

(60) Provisional application No. 60/531,645, filed on Dec. 22, 2003.

(51) Int. Cl.
| C12M 1/36 | (2006.01) |
| C12M 1/38 | (2006.01) |
| C12M 3/00 | (2006.01) |
| C12M 1/34 | (2006.01) |

(52) U.S. Cl. ........................ 435/286.7; 435/3; 435/7.25; 435/286.1; 435/287.2; 435/288.6; 436/513; 436/518; 436/520; 436/523; 436/524; 436/527; 436/528; 436/535; 436/539; 436/17; 436/18; 436/165; 436/177; 436/178; 436/179; 422/73

(58) Field of Classification Search ..................... 435/2, 435/7.25, 40.51, 286.7, 288.6, 3, 286.1, 287.2; 436/513, 520, 527, 538, 17, 18, 63, 165, 436/175, 177, 178, 179, 506, 518, 523, 524, 436/528, 535, 539; 422/101, 73

See application file for complete search history.

(56) References Cited

U.S. PATENT DOCUMENTS

| 2,770,572 A |   | 11/1956 | Eldon |
| 2,850,430 A |   | 9/1958  | Nelson |
| 3,074,853 A |   | 1/1963  | Brewer |
| 3,272,319 A |   | 9/1966  | Brewer |
| 3,424,558 A |   | 1/1969  | Eldon |
| 3,502,437 A |   | 3/1970  | Mass |
| 3,666,421 A |   | 5/1972  | Price |
| 5,338,689 A |   | 8/1994  | Yves et al. |
| 5,512,432 A |   | 4/1996  | Lapierre et al. |
| 5,552,064 A | * | 9/1996  | Chachowski et al. ........ 210/787 |
| 5,650,068 A |   | 7/1997  | Chachowski et al. |
| 5,863,802 A |   | 1/1999  | Yves et al. |
| 6,114,179 A |   | 9/2000  | Lapierre et al. |

FOREIGN PATENT DOCUMENTS

| EP | 0 104 881 A2 | 4/1984 |
| EP | 0104801 A2   | 4/1984 |
| EP | 0485228 B1   | 5/1992 |
| EP | 0725276 B1   | 8/1996 |
| EP | 0755719 B1   | 1/1997 |

OTHER PUBLICATIONS

Novaretti et al., Comparison of conventional tube test with diamed gel microcolumn assay for anti-D titration, Clin. Lab. Haem. 25: 311-315 (2003).*
Byrne et al., A Comparison of two column agglutination technologies for routine antibody screening using the indirect antiglobulin technique, British Journal of Biomedical Science 53: 193-195 (1996).*
International Search Resort dated Apr. 19, 2005 for corresponding PCT/US2004/042531.
Blaney, K., and Howard, P., "Basic and Applied Concepts of Immunohematology", St. Louis, 2000, Mosby, Literature Info Cover.
Issitt, P.D., and Anstee, D.L., "Applied Blood Group Serology", Ed 4, Durham, NC 1998, Montgomery Scientific Publications, Literature Info Cover.
Kaplan, L., and Pesce, A., "Clinical Chemistry: Theory, Analysis, and Correlation", St. Louis, 1984, Mosby.
Löw, B. and Messeter, L., "Antiglobulin Test in Low-Ionic Strength Salt Solution for Rapid Antibody Screening and Cross Matching", *Vox Sang*, 26:53-61, 1974.
Malyska H., and Weiland, D., "The Gel Test", *Lab Med*, 25:81-85, 1994.
Vengelen-Tyler V, "Technical Manual", Ed. 12, Bethesda, MD 1996, American Association of Blood Banks, Literature Info Cover.
Byrne T. et al., "A comparison of two column agglutination technologies for routine antibody screening using the indirect antiglobulin technique", British Journal of Biomedical Science, vol. 53, No. 3, 1996, pp. 193-195.
Luhong Tang et al., "A kinetic study of the synthesis of ascorbate fatty acid esters catalyzed by immobilized lipase in organic media", Biotechnology and Applied Biochemistry, vol. 32, No. 1, Aug. 2000, pp. 35-39.
Novaretti M C Z et al., "Comparison of conventional tube test with diamed gel microcolumn assay for anti-D titration". Clinical and Laboratory Haematology, vol. 25, No. 5, Oct. 2003, pp. 311-315.
Crowther, John R.,"The Elisa Guidebook", 2001, Humana Press.
Ludewig, S., and Chautin, A., "Factors Influencing the Agglutination of Red Blood Cells, Red Blood Cell Stroma, and Lymphocytes", J. Biol. Chem, vol. 179, 1949, pp. 271-278.

* cited by examiner

*Primary Examiner*—Gailene R Gabel

(57) ABSTRACT

Methods for reducing time to result in blood bank diagnostic testing with an agitation device and a low ionic strength solution are disclosed. Specifically provided are methods for reducing incubation time for antigen-antibody reactions in an immunohematologic assay by subjecting the assay reactants to incubation with agitation and optionally additionally a low ionic strength diluent.

8 Claims, No Drawings

REDUCING TIME TO RESULT FOR BLOOD BANK DIAGNOSTIC TESTING

CROSS REFERENCE TO RELATED APPLICATIONS

This application is a non-provisional application claiming priority from a provisional application U.S. Ser. No. 60/531,645 filed Dec. 22, 2003 and the National Stage Serial Number PCT/US04/42531 filed Dec. 17, 2004.

BACKGROUND OF THE INVENTION

This invention relates to the field of agglutination assays to detect the binding of ligands, and particularly immunological binding (antigen and antibody binding) such as that involved in blood group serology ("immunohematology").

Immunohematology requires the determination of blood cell compatibility between a blood donor and a patient recipient before a transfusion or organ transplant involving the patient. Blood cell compatibility is determined by the non-occurrence of an immunological reaction between antibodies contained in the blood serum of a patient and antigens present on blood cells from the donor.

Many different blood group antigens are found on the surface of the red blood cells of every individual. These antigens, the products of inherited genes, exist in a unique combination in everyone except identical twins. Blood grouping is generally the process of testing red cells to determine which antigens are present and which are absent, normally utilizing antibodies to the antigen tested for.

Additionally, when a person does not have a particular red cell antigen on his or her red blood cells, his or her serum may contain antibody to that antigen. Whether or not the antibody is present in the serum depends on whether the person's immune system has been previously challenged by, and responded to, that specific antigen or something very similar to it. For example, a person whose red blood cells are Type A, i.e. having "A" antigens on the red cells, will have anti-B antibodies in his or her serum. Thus, if such a person is given type B blood, an immunological reaction will occur with possible serious clinical consequences.

As an additional consideration, it should be noted that the human body is constantly exposed to antigens in pollens, food, bacteria and viruses. Some of these "natural" antigens are apparently so similar to human blood group antigens that they stimulate almost every susceptible person to produce antibodies. Thus, certain antibodies are expected in the serum of anyone whose red cells lack the reciprocal antigen. This is especially true of the ABO system. Accordingly, a second confirmatory test is often performed on the patient/donor sera. The test for expected antibodies of the ABO blood group system in sera is called "reverse" or "indirect" blood grouping, whereas the test for antigen on patient red blood cells ("RBCs") is referred to as "forward" or "direct" testing.

Since the early 1900's, the general approach, known as the "Landsteiner" method, has been to add a patient's red blood cells to a standard laboratory test tube containing a blood group antibody (such as Anti-A or Anti-B) mix to allow antibody/antigen binding reactions to take place, and then to centrifuge. If the antigen tested for is present, the antibody/antigen binding will have taken place resulting in agglutination of the patient's red blood cells. The test tube is manually shaken to dislodge the centrifuged button of "clumped" cells at the bottom. A subjective determination is then made as to whether or not the dislodged cells are "clumped", and to what extent.

During the mid-1900's, attempts were made to simplify this technique to minimize the subjective nature of the test and to reduce mistakes. It was recognized that a somewhat permanent record of the results of compatibility testing could be had by employing wettable, either non-absorbent, or in some cases absorbent, test slides or test cards having the requisite immunochemical reagents on at least a portion of their surfaces. U.S. Pat. Nos. 2,770,572, 2,850,430, 3,074,853, 3,272,319, 3,424,558, 3,502,437 and 3,666,421, and European Patent Application #0 104 881-A2 depict select examples of such test cards and related apparti.

It is standard bloodbanking practice to test for A, B and D ($RH_o$) antigens on a sample of a person's blood (and to perform tests for other antigens in selected cases), and to crosscheck the results by testing the person's sera to determine the acquired antibodies that might be present. The former is referred to as "forward typing" or "direct test" while the latter is referred to as "reverse typing" or "indirect test". The results from each of these typing exercises have to agree.

For the reverse or indirect test, for detecting antibodies in the serum or plasma of a patient, reagents containing blood cells having known antigens are mixed with a patient serum sample. The reactants are incubated for a period of time sufficient to permit agglutination of the red blood cells, which occurs when antibodies against those antigens are present. Such incubation typically ranges from about 10 minutes to about 40 minutes in modern testing. The mixture is then centrifuged, and if agglutinated blood cells are present, such agglutinates are clearly visible at the bottom of the reaction vessel, thus indicating the presence of antibodies in the sample directed against the known antigens on the red blood cells. If no antibodies are present in the sample directed against the known antigens on the red blood cells, agglutination does not occur, and this is indicated by the absence of agglutinated red cells after centrifugation.

Antibodies of the ABO blood grouping system are generally immunoglobulin M (IgM). These antibodies have ten antigen binding sites per molecule. The IgM antibody is large enough to span the distance between red blood cells, so that when they are centrifuged, the cells will be bound together in a lattice "cell-antibody-cell-antibody" and will remain clumped together in agglutinates. For example, if anti-A is added to blood group A or blood group AB cells and the mixture is centrifuged, the cells will remain in clumps when resuspended. With the same antibody, group O and group B cells will resuspend as individual cells. Agglutination facilitated by IgM antibodies is termed direct agglutination.

Anti-D antisera is now manufactured as monoclonal IgM or polyclonal IgG mixtures. These reagents can phenotype RBCs on immediate spin without the presence of high protein additives. The human IgG molecule was also chemically modified to unhinge the disulfide bond so it could have a larger span and act like a IgM molecule.

IgG antibodies cannot easily span the distance between cells which tend to repel each other in a saline environment. Thus, IgG will bind to red cell antigens matching its specificity, but will not directly agglutinate such red cells as effectively as the larger IgM antibodies will. The presence of IgG antibody bound to a red cell is thus usually detected by the addition of anti-IgG which will cause the requisite agglutination, resulting in a lattice of "red cell-IgG/Anti-IgG/IgG-red cell".

Serum naturally contains IgG that will neutralize the anti-IgG antibody added to bind to red blood cells. Therefore, the serum must be removed before such anti-IgG is added to the cells. Tests for IgG bound to red cells in vivo are called direct antiglobulin tests. Tests for IgG bound to red cells in vitro are called indirect antiglobulin tests. Such antiglobulin tests are also called "Coombs" tests. This indirect antiglobulin test is a blood test used to determine whether there are IgG antibodies in a patient's serum to specified antigens on the surface of red blood cells. In the Coombs test, serum is incubated in the presence of reagent red cells to allow the antibodies to bind to antigens on the surface of the red cells. These IgG antibodies most often do not, by themselves, agglutinate the red cells, or only agglutinate them insufficiently to be detected visually by conventional techniques. Addition of a second antibody directed to human IgG is usually necessary to facilitate visible agglutination.

A convenient gel test and method of detecting antibodies or antigens is contemplated in this invention, wherein complexes of carrier-bound antibodies with antigens or carrier-bound antigens with antibodies in aqueous medium are made optically visible as before described. The carrier is preferably a gel or polymer and the antigens or antibodies as the case may be are bound to the carrier surface. The gel test contemplated herein is the Anti-Human Globulin Anti-IgG (Rabbit) MTS Anti-IgG Card™ for use with the ID-Micro Typing System™ (Micro Typing Systems, Inc., Pompano Beach, Fla., as disclosed in U.S. Pat. Nos. 5,338,689, 5,512,432, 5,863,802, and 6,114,179, the contents of which are incorporated herein by reference. Such a card may be used for both Direct and Indirect Antiglobulin Test. However, the invention is not limited to such test system and method but may be used with other formats besides gel such as for example, test tube, slide, solid phase and column agglutination technology (CAT) systems and methods, the latter whether in column or cassette form such as for instance the BioVue System™ of ortho-Clinical Diagnostic Systems, Inc., Raritan, N.J., and might be used in any immunohematology system that employs incubation of the antibody and red cell antigen, regardless of test method.

In the ID-Micro Typing System™, the Direct test, which does not normally employ incubation, is accomplished by the employment of a gel card containing microtubes each of which contain an antibody incorporated into the gel matrix, and wherein diluted patient RBCs are placed on top of the gel carrier. Anti-human globulin (anti-IgG) is present in the gel. The card is centrifuged, which accelerates the reaction, if any, between the antibody reagent on the gel and the patient blood cells containing antigen, and also urges any cells toward the bottom of the microtubes. The gel in the microtubes act as a filter, however, and resist or impede downward movement of the particles in the microtube. As a result, the nature and distribution of the particles in the microtube after centrifuging provides a visual indication of whether any agglutination reaction occurred in the microtube, and if so, of the strength of that reaction.

If no agglutination reaction occurs, then all or virtually all of the red blood cells in the microtube pass downward during centrifuging, to the bottom of the microtube and form a pellet at the bottom. If there is a very strong reaction between the reagent and the red blood cells, virtually all of the red blood cells agglutinate, and large agglutinates form at the top of the microtube, above the gel contained therein; the gel or glass beads prevent the agglutinates from passing, during centrifuging, to the bottom of the column, so that after centrifuging the agglutinates remain on the surface of the gel.

If there is a reaction between the reagent and the blood cells, but this reaction is not as strong as the above described very strong reaction, then some but not all of the red blood cells agglutinate. The percentage of red blood cells that agglutinate and the size of the agglutinated particles both vary directly with the strength of the reaction. During centrifuging, the unreacted blood cells pass to the bottom of the column, and the distance that the agglutinated particles pass downward through the column depends on the size and number of those particles. Hence, the size of the pellet of red blood cells at the bottom of the microtube, and the extent to which the agglutinates penetrate into the gel in the microtube, are both inversely related to the strength of the reaction between the reagent and the red blood cells.

The instant invention is a method to reduce time to result in blood bank immunohematologic testing for tests that use incubation of the antibody and the red cell antigen. As discussed hereinabove, antigen-antibody reactions, including red cell typing reactions needing a incubation step, in immunohematology are detected by the visible agglutination of red blood cells or the evidence of hemolysis at the completion of testing. Such a test is for example, the Indirect or Reverse test as before mentioned, wherein patient antibodies are detected in sample plasma or serum by agglutination with diluted reagent RBCs. As stated, and in the ID-MTS System™ when for example conducting the Indirect test, patient sample plasma or serum is added to a microtube containing reagent RBCs that have been diluted in a low ionic strength solution (diluted MTS Diluent 2™), the card containing the microtube is incubated with agitation, followed by centrifugation and removal and reading of the card for agglutination. The instant invention allows for a decreased time for incubation due to potentiation of the antibody-antigen reaction as discussed below.

In the sensitization stage of hemagglutination, the antibody attaches to an antigen on the red blood cell. During this immunologic recognition stage antigenic determinants on the red blood cell combine with the antigen-binding site of the antibody molecule. The combination of an antigen and antibody is a random pairing of the two molecules determined largely by chance. Several factors influence the probability for this collision of antigen and antibody (Blaney K, Howard P: Basic and Applied Concepts of Immunohematology, St Louis, 2000, Mosby, and Vengelen-Tyler V: Technical manual, ed 12, Bethesda, Md., 1996, American Association of Blood Banks), and include the following:

Concentrations of Antibody and Antigen

The relative serum to cell ratio (i.e., the ratio of antigen on the red blood cell to antibody in the serum) will influence the probability of antigen-antibody combinations. Increasing the amount of serum in testing increases the concentration of antibodies available for binding to the red blood cell antigens. The number of antigen sites available on a per red blood cell basis also contributes to the strength of the antigen-antibody reaction.

Antigen Receptor Accessibility

The position of an antigen relative to the lipid bilayer of the red blood cell membrane contributes to its accessibility to antibody molecules, particularly IgG molecules. If the steric hindrance is decreased, the antibody molecules have a greater opportunity of interaction with the antigenic determinants.

Temperature of the Reaction Milieu

The temperature of the reaction influences the first stage of the agglutination reaction. In immunohematology most antibodies with clinical relevance are IgG immunoglobulins, which optimally react at temperatures of 37° C. In contrast, IgM antibodies are more reactive at lower temperatures, generally at or below room temperature. Providing the suitable temperature in the reaction enhances the sensitization step.

Incubation Time

Allowing adequate time for the combination of antigen and antibody to attain equilibrium is also a factor that enhances the first stage of the agglutination reaction.

pH

The optimal pH for hemagglutination is approximately pH 7.0. This pH is adequate for the majority of important red blood cell antibodies.

Ionic Strength

The lowering of the ionic strength of the test medium greatly enhances the rate at which antibodies bind to red blood cells. The use of low ionic strength solution as a potentiator of agglutination is a common practice in blood bank testing. For example, use of a buffer of about 0.03M is most useful. See Low and Messiter, Vox Sang 1974, Vol. 26, p. 53. Use of MTS Diluent 2™ (Micro Typing Systems, Inc., Pompano Beach, Fla.) is preferred.

All current commercial antibody detection test methodologies have the initial step of having the antigen (RBC) and the antibody (serum or plasma) incubated at 37° C. for a period of time, between 10-40 minutes and typically 15 minutes. The instant invention provides for a significant reduction of time of incubation in an immunohematologic assay by employing continuous agitation and optionally, low ionic strength diluent. This reduction of test time can be realized no matter what specific test format is being used, whether test tube test, slide test, solid phase test system, microcolumn or microtube, or microplates, and regardless of matrix material, for instance, whether gel or glass bead is employed as matrix.

Blood bank testing has maximized the use of the factors previously outlined to produce diagnostic tests with appropriate sensitivity and specificity. The manipulation or combination of any of these variables of antigen-antibody reactions in test systems can reduce the time to result in blood bank testing. The instant invention is directed to reduction in incubation time required by use of continuous agitation while incubating. However, it will be understood that the actual amount of reduction in time can vary with the factors enumerated hereinabove, such as the ionic strength of the diluent, the presence or absence of enhancement agents (such as bovine albumin, polyethylene glycol, or proteolytic enzyme) the red blood cell/serum or plasma ratio, the initial temperature of the test sample and reagents, etc.

A review of the literature has not identified the previous use or disclosure of continuous agitation as a means to reduce the incubation time in immunohematology.

SUMMARY OF THE INVENTION

The present invention provides a method and device for reducing time to result in blood bank diagnostic testing, using agitation and in a preferred embodiment, a low ionic strength buffer.

In a preferred embodiment, the invention can employ a device that is an incubation chamber and agitation block which can accommodate one or more containers, for example agglutination sample test tubes, slides or the ID-Micro Typing Systems™ gel cards containing microtubes as discussed above. The container is centrifuged and the presence or absence of agglutinates detected.

In one preferred embodiment of the invention there is provided a method for reducing time to result in immunohematology assays, comprising performing an Indirect test comprising:

(a) incubating a sample with antigen positive reagent RBCs at 37° C. with continuous agitation;

(b) centrifuging the sample in an anti-IgG matrix (the Anti-IgG as either supplied within the matrix or added as a reagent) for 10 minutes; and (c) reading the result.

Such method includes wherein the sample is plasma or serum. The continuous agitation is provided by a mechanical agitation block or manually. The anti-IgG matrix comprises for example gel beads. Preferably the anti-IgG matrix is disposed in a test tube or microtube of the ID-Micro Typing System™.

In one embodiment, the antigen-positive RBCs in step (a) are admixed with a low ionic strength diluent such as for example a hypotonic buffered solution employing buffers commonly used in the art such as for example HEPES and TRIS. Preferably the low ionic strength diluent is less than about 0.03M.

When the immunohematologic technology used comprises microtubes disposed in gel card form, such as in the ID-Micro Typing System™, the invention in a preferred embodiment comprises a method for performing an Indirect test comprising:

(a) providing a microtube containing an upper chamber and a lower chamber which contains an anti-IgG-containing matrix for separating agglutinated from non-agglutinated cells;

(b) adding antigen positive RBCs to a test tube;

(c) adding patient plasma or serum to the test tube;

(d) incubating the product of the admixture of steps (b) and (c) at 37° C. with continuous agitation for 2-15 minutes;

(e) adding the incubated admixture of step (d) to the microtube and centrifuging the microtube; and (f) reading the result.

In the aforementioned method, the sample is plasma or serum. The continuous agitation is provided by a mechanical agitation block or it may be provided manually. As before mentioned, the test red blood cells in step (b) are admixed with a low ionic strength diluent of less than about 0.03 M.

In yet a further embodiment of the invention, there is contemplated the use of column agglutination technology, specifically the BioVue™ column (Ortho-Clinical Diagnostics, Inc., Raritan, N.J.) using the methods of the current invention. The methods employed in BioVue™ are described in detail in EP 485,228, EP 755,719, EP 725,276, U.S. Pat. Nos. 5,650,068, 5,552,064, and disclose in place of a microtube, a reaction vessel comprising a microcolumn having a separation region and an incubation region wherein the separation region contains a matrix for separating agglutinated cells from unagglutinated cells. The method involves the similar mechanism of detecting the presence or absence of antibodies or antigens, preferably blood group antibodies or antigens by (a) adding an antibody or antigen detecting reagent and a liquid patient sample possibly containing an antibody or antigen, to the matrix which permits movement of non-agglutinated reactants but does not permit movement of agglutinated reactants; (b) applying a force to the matrix, for example centrifugal force, to effect movement through the matrix; and (c) detecting the presence or absence of agglutinated reactants.

In particular, there is further disclosed a method for reducing time to result in immunohematology assays, comprising:

(a) providing a microcolumn containing an upper chamber and a lower chamber which contains a matrix for separating agglutinated from non-agglutinated cells;

(b1) depositing reagent red cells and patient serum or plasma sample to the upper chamber of the microcolumn; or (b2) depositing a reagent antibody with known specificity for red cell antigen and a patient red cell sample;

(c) incubating the microcolumn of (b1) or (b2) at 37° C. with continuous agitation for 2-15 minutes;

(d) centrifuging the microcolumn; and (e) reading the result.

As before mentioned, the continuous agitation is provided by a mechanical agitation block or manually. The red blood cells in step (b) may be admixed with a low ionic strength diluent of preferably less than about 0.03M. Preferably the low ionic strength diluent is MTS Diluent 2™ (Micro Typing Systems, Inc., Pompano Beach, Fla.) that has itself been diluted to less than about 0.03M.

DETAILED DESCRIPTION

This invention describes a method that uses a device or combination of devices and methods, to significantly reduce the incubation time required to accomplish the antigen-antibody binding (sensitization stage) in IgG-dependent red blood cell antibody reactions that employ an incubation step. The device and method employs continuous agitation during incubation, with simultaneous heating, to decrease the incubation time. It changes the rate of an antigen-antibody reaction through the increased movement of molecules in the reaction milieu, which increases the surface area for collisions between appropriate antigenic determinants and antibodies (Kaplan L, Pesce A: Clinical chemistry: theory, analysis, and correlation, St Louis, 1984, Mosby). This method can be used in combination with a low ionic strength red blood cell diluent, which may be used to dilute the antibody screening cells prior to testing.

The agitation method may be used in all immunohematologic technologies and formats whether test tube test, slide test, solid phase test system, microcolumn or microtube, or microplates, and regardless of matrix material, for instance, whether gel or glass bead is employed as matrix. The method may be conducted using any device that may take the form for example of a mechanical agitation "block" or may be accomplished by a manual shaking/agitation.

The incubation may be accomplished through use of an electric incubator device or other means such as a water bath.

When employing gel as the matrix (Malyska H, Weiland D: The gel test, Lab Med 25:81-5, 1994), in the ID-Micro Typing System™ (Micro Typing Systems, Inc., Pompano Beach, Fla.), the implementation of the agitation device in combination with the low ionic strength red blood cell diluent reduced the incubation time from 15 minutes to 2 minutes in the samples tested. This reduction is significant in the performance of an indirect antiglobulin test. In routine practice, the shortest incubation time for indirect antiglobulin testing is typically between 10-15 minutes. In indirect antiglobulin testing the incubation period is included to allow sufficient antibody uptake on the red blood cells for detection with antiglobulin reagents. Using solutions with normal (physiologic) ionic strength, indirect antiglobulin tests use a specified incubation time between 15 and 60 minutes. Serologic studies have concluded that most antibodies are attached to the red blood cells after 15 minutes of incubation for detection in this antiglobulin testing format (Issitt P D, Anstee D L: Applied blood group serology, ed 4, Durham, N.C., 1998, Montgomery Scientific Publications). With the introduction of low ionic strength solutions in immunohematology, the uptake of antibody by red blood cells occurred more rapidly than observed in a normal ionic strength solution. Such low ionic strength solutions include those as disclosed by Low and Messiter, ibid. and MTS Diluent 2™ (Micro Typing Systems, Inc., Pompano Beach, Fla.). In an even lower ionic strength system such as that contemplated in the present invention, the incubation times can be reduced in the performance of indirect antiglobulin testing to 10-15 minutes. Consequently, an agitation-incubation device combined with a low ionic strength red blood cell diluent maximizes antibody uptake on red cells and can significantly reduce the incubation time in indirect antiglobulin testing procedures. Such low ionic strength solution is typically less than 0.03M concentration.

Currently, antibody detection procedure for the ID-Micro Typing System™ Gel Test requires a 15-minute incubation period at 37° C. See, for example package insert for Anti-IgG (Rabbit) MTS Anti-IgG Card™ used in the gel test In parallel testing of continuous agitation versus no agitation during incubation using the ID-Micro Typing System™ Gel Test, continuous agitation of test reagents and samples during incubation time was tested and compared to no agitation. These tests (see Examples) demonstrated that equivalent serologic reactions were obtained at 4 minutes with agitation versus 10 minutes with no agitation. Therefore, it was demonstrated that the time to result for the ID-Micro Typing System™ Gel Test can be reduced by 11 minutes for a 60% reduction in time to result.

The agitation-incubation device may consist of an incubation chamber that maintains an environment at a temperature of 37° C. and an agitation block. The agitation block is powered by an external power source. The incubator used in the prototype model was a Thermolyne Model 142300 (Barnstead International, Dubuque, Iowa). However, the agitation block can be adapted to any incubation chamber for accommodation in any system that applies the use of the agitation block in a test platform.

The agitation block is connected to the external power source, which controls the rate of mixing during incubation. The agitation block is designed to hold test tubes and/or cards, and can be physically removed from the incubation chamber. Empty test tubes/cards are kept in the agitation block to maintain a pre-test temperature of 37° C. The agitation block is removed from the incubation chamber prior to the addition of test reactants. The test reactants (i.e., red blood cells and plasma/serum) are manually added to the test tubes/card microtubes outside the incubation chamber. A pre-labeled tube/card is also placed in a pre-drilled groove on the agitation block. Colored line guides, embedded in the agitation device, assist in the alignment of the test tubes/cards. After adding the test reactants, the agitation block is then returned to the incubation chamber and is turned on to allow the mixing of the test reactants for a period of time, for example, from about 2 minutes, at the predetermined agitation rate, whether in a rotary or reciprocal agitation motion and in either case at a speed in accordance with that typically used by one having ordinary skill in the art of agitating such admixtures. Upon completion of the incubation period the agitation block is removed from the incubation chamber. The test reactants are added to the tubes/card microtubes. The tube/card is placed in an appropriate centrifuge and centrifuged sufficient to advance any agglutinates formed to the bottom of the tube/microtube of the card.

A six-tube agitation block design was selected to accommodate the six test tubes. The design of the agitation block can be configured to meet the requirements for other test technologies and automation platforms. Alternative agitation block designs can accommodate any other appropriate vessel for mixing purposes. Similarly, alternative centrifuge designs can accommodate any other appropriate vessel for centrifugation purposes.

A red blood cell diluent with a reduced ionic strength may be used to further enhance the rate of antibody uptake on the test cells. The MTS Diluent 2™, designed for antiglobulin testing in the ID-Micro Typing System™ Gel Test, was diluted with deionized water as described hereinbelow, in initial timed studies and evaluated for increased antibody uptake. The results of this study determined the optimal dilution of MTS Diluent 2™ for the test system. The low ionic strength red blood cell diluent's final formulation was designed with the following proportions:

7 ml of Deionized water was added to 10 ml of ID-MTS Diluent 2™.

STAT Indirect Antiglobulin Procedure—Gel Test

The indirect antiglobulin procedure that capitalizes on maximizing the test advantages of combining agitation and low ionic strength solutions uses the following testing protocol for a gel test application. All reagents and samples are brought to room temperature prior to use. Sample requirements include EDTA plasma. The screening cells are diluted to a concentration of 0.4% in the low ionic strength diluent prior to use.

The agitation block containing the six preheated tubes is removed from the agitation-incubation device.

An Anti-IgG ID-Micro Typing System™ gel card is labeled with appropriate patient/test information and is placed in the holder on the agitation block. The appropriate microtubes of the labeled card are aligned in front of their corresponding test tubes. Colored lines are embedded on the agitation block for alignment guides. A volume of the appropriate 0.4% screening cell is pipetted into a tube, followed by addition of the patient's EDTA plasma pipetted into screening cell tubes. Agitation power is turned on. Agitation proceeds for 2 minutes and automatically shuts down. The agitation block is removed from the incubator. A volume of test sample is added to the appropriate microtube card from the corresponding test tube. The card is centrifuged for 10 minutes in an MTS centrifuge (Micro Typing Systems, Inc., Pompano Beach, Fla.).

It should be noted that the ionic strength of the red blood cell diluent, incubation temperatures, and the agitation rate are variables in the above procedure and can be altered and still achieve a reduction of incubation time.

There are several important practical advantages to blood bank diagnostics in use of the instant invention. For example, time to result in emergency testing is shortened (i.e., STAT orders), the process is applicable to blood bank automation platforms, the time to result is shortened for both automation and manual testing, and the process is applicable to all existing blood bank technologies and formats: gel, tube, and solid phase.

Throughout this application, various patents and papers are referenced. The disclosures thereof in their entireties are hereby incorporated by reference into this application in order to more fully describe the state of the art as known to those skilled therein as of the date of the invention described and claimed herein.

The following examples are provided for the purposes of illustration only and are not to be viewed as a limitation of the scope of the invention.

EXAMPLES

Example 1

STAT Indirect Antiglobulin Procedure

Gel Test Employing Test Tube Format

All reagents and samples were brought to room temperature prior to use. The sample requirements includes use of EDTA plasma. Screening cells were diluted to a concentration of 0.4% in the low ionic strength diluent, which was 10 mL of the MTS Diluent 2™ further diluted in 7 ml of deionized water. The agitation block containing the six preheated tubes was removed from the agitation-incubation device. An ID-MTS Anti-IgG (Rabbit) Gel Card was labeled with appropriate patient/test information and placed in the holder on the agitation block. The appropriate microtubes of the labeled gel card were aligned in front of their corresponding test tubes. Colored lines were embedded on the agitation block for alignment guides. 200 µl of the appropriate 0.4% screening cell (as diluted above) was pipetted into a tube. 100 µl of the patient's EDTA plasma was then pipetted into screening cell tubes. Agitation power was turned on. Agitation proceeded for 2 minutes and automatically shut down. The agitation block was removed from the incubator. 150 µl of the test sample was added to the appropriate microtube on the gel card from the corresponding test tube. The card was centrifuged for 10 minutes at 900 rpm in the MTS centrifuge.

Example 2

Effects of Agitation vs. No Agitation in the ID-MTS Gel Test

Part A—Incubation at 37° C. with Agitation

A patient plasma sample with anti-D present was serially diluted. 25 µL of serially diluted plasma was combined with 50 µL of 0.8% of D-antigen positive RBCs diluted in MTS Diluent 2 in a test tube. The sample was incubated with agitation at 37° C. in a water bath. 75 µl were added to an Anti-IgG ID-MTS Gel Card™ and centrifuged in a MTS centrifuge for 10 minutes at 900 rpm. The maximum titration point was measured serologically. The time to reach maximum titer was 4 minutes.

Results are tabulated at Table 1. The Maximum Titer column is reported as "8" as maximum agglutination results were achieved with the 1:8 dilution of the sample.

Part B—Incubation at 37° C. with No Agitation

The materials and procedures of Part A were repeated with the exception that the sample was not agitated. The time to reach maximum titer was 10 minutes.

Results are tabulated at Table 1. The Maximum Titer column is reported as "8" as maximum agglutination results were achieved with the 1:8 dilution of the sample.

Part C—Incubation at Room Temperature with Agitation

The materials and procedures of Part A were repeated with the exception that the sample was incubated at room temperature (about 18-25° C.). The time to reach maximum titer was 15 minutes.

Results are tabulated at Table 1. The Maximum Titer column is reported as "8" as maximum agglutination results were achieved with the 1:8 dilution of the sample.

Part D—Incubation at Room Temperature with No Agitation

The materials and procedures of Part A were repeated with the exceptions that the sample was incubated at room temperature (about 18-25° C.), and that the sample was not agitated. The time to reach maximum titer was 20 minutes.

Results are tabulated at Table 1. The Maximum Titer column is reported as "8" as maximum agglutination results were achieved with the 1:8 dilution of the sample.

It will be noted that agitation decreased the time required for incubation from the standard ID-MTS procedure as contained on the package insert by 11 minutes at 37° C.

TABLE 1

| Conditions | Maximum Titer | Time to Reach Maximum Titer |
|---|---|---|
| 37 C. Incubation - Mixing | 8 | 4 minutes |
| 37 C. Incubation - No Mixing | 8 | 10 minutes |
| RT Incubation - Mixing | 8 | 15 minutes |
| RT Incubation - No Mixing | 8 | 20 minutes |

Example 3

STAT Indirect Antiglobulin Procedure—Gel Test Employing Gel Card Format

All reagents and samples are brought to room temperature prior to use. The sample requirements include use of EDTA plasma. Screening cells are diluted to a concentration of 0.4% in the low ionic strength diluent, (which is 10 mL of the MTS Diluent 2™ further diluted in 7 ml of deionized water). The agitation block containing the pre-heated ID-MTS Anti-IgG (Rabbit) Gel Card which is labeled with appropriate patient/ test information, is removed from the agitation-incubation device and is placed in the holder on the agitation block. Colored lines are embedded on the agitation block for alignment guides. 200 μl of the appropriate 0.4% screening cell (as diluted above) is pipetted into a microtube of the gel card. 100 μl of the patient's EDTA plasma is then pipetted into the screening cell microtube. Agitation power is turned on. Agitation proceeds for 2 minutes and automatically shuts down. The agitation block is removed from the incubator. 150 μl of the test sample is added to the appropriate microtube on the gel card. The card is centrifuged for 10 minutes at 900 rpm in the MTS centrifuge.

The agglutination result is then read.

It will be understood by those skilled in the art that the foregoing description and examples are illustrative of practicing the present invention, but are in no way limiting. Variations of the detail presented herein may be made without departing from the scope and spirit of the present invention.

We claim:

1. A method for reducing time to result in the form of agglutination in immunohematology assays, comprising:
    (a) incubating a sample with antigen positive red blood cells ("RBCs") admixed with a low ionic strength diluent at 37° C. for from 2 minutes to 15 minutes with continuous agitation;
    (b) centrifuging the product of the admixture in step (a) in an anti-IgG matrix for 10 minutes; and
    (c) reading the result in the form of agglutination.

2. The method of claim 1 wherein the sample is plasma or serum.

3. The method of claim 1 wherein the continuous agitation is provided by a mechanical agitation block.

4. The method of claim 1 wherein the continuous agitation is provided manually.

5. The method of claim 1 wherein the anti-IgG matrix comprises a gel.

6. The method of claim 1 wherein the anti-IgG matrix comprises glass beads.

7. The method of claim 1 wherein the anti-IgG matrix is disposed in a microtube.

8. The method of claim 1 wherein the diluent has a low ionic strength of less than about 0.03 M.

* * * * *